(12) United States Patent
Sauska et al.

(10) Patent No.: US 7,173,254 B2
(45) Date of Patent: Feb. 6, 2007

(54) COMPACT GERMICIDAL LAMP HAVING MULTIPLE WAVELENGTHS

(75) Inventors: Christian Sauska, Orange, CT (US); Arpad Pirovic, Woodbridge, CT (US)

(73) Assignee: Light Sources, Inc., Orange, CT (US)

( * ) Notice: Subject to any disclaimer, the term of this patent is extended or adjusted under 35 U.S.C. 154(b) by 405 days.

(21) Appl. No.: 10/849,375

(22) Filed: May 19, 2004

(65) Prior Publication Data

US 2005/0258763 A1 Nov. 24, 2005

(51) Int. Cl.
*H01J 13/46* (2006.01)

(52) U.S. Cl. .................. 250/455.11; 313/493; 313/490

(58) Field of Classification Search ............... 313/490, 313/493; 250/455.11
See application file for complete search history.

(56) References Cited

U.S. PATENT DOCUMENTS

| | | | | |
|---|---|---|---|---|
| 4,545,774 A * | 10/1985 | Van Gils et al. ............... | 445/22 |
| 5,003,220 A * | 3/1991 | Fohl et al. .................. | 313/488 |
| 5,294,867 A * | 3/1994 | Grossman .................... | 313/490 |
| 6,417,615 B1 * | 7/2002 | Yasuda et al. ............... | 313/490 |
| 6,657,375 B2 * | 12/2003 | Goud .......................... | 313/493 |
| 6,664,726 B2 * | 12/2003 | Magai ........................ | 313/493 |
| 6,719,465 B2 * | 4/2004 | Earle et al. ................. | 396/625 |
| 6,771,024 B2 * | 8/2004 | Sudou et al. ................. | 315/56 |

* cited by examiner

*Primary Examiner*—David A. Vanore
(74) *Attorney, Agent, or Firm*—Fattibene & Fattibene; Paul A. Fattibene; Arthur T. Fattibene

(57) ABSTRACT

A compact germicidal lamp having a plurality of adjacent parallel glass cylinders capable of transmitting different wavelengths of ultraviolet radiation connected by a perpendicular glass tube. A first glass cylinder made of a doped quartz material and capable of transmitting ultraviolet radiation in the wavelength range of approximately 254 nanometers is positioned adjacent a second glass cylinder made of a quartz material capable of transmitting ultraviolet radiation in the wavelength range of approximately 185 nanometers. The first and second glass cylinders are connected by a perpendicular glass tube. The compact germicidal lamp, when used in a germicidal system, provides effective germicidal action in a small space. The germicidal lamp of the present invention is more easily manufactured than prior germicidal lamps and can be made having a high power.

15 Claims, 3 Drawing Sheets

COMPACT GERMICIDAL LAMP HAVING MULTIPLE WAVELENGTHS

FIELD OF THE INVENTION

The present invention relates in general to germicidal lamps used in the treatment of wastewater, and more particularly to a germicidal lamp that is compact in size and provides at least two different wavelengths of ultraviolet radiation.

BACKGROUND OF THE INVENTION

Gas discharge lamps are often used to produce ultraviolet radiation at wavelengths suitable for killing small microbes or germs. Ultraviolet radiation has been used to kill microorganisms by destroying their DNA. Germicidal protection using ultraviolet radiation is a safe and proven technology that helps kill bacteria, mold spores and viruses. The band of wavelengths that provide a germicidal action is often referred to as UVC, and is generally in the range of 250 nanometers. It is often desirable to produce a germicidal lamp that has the capability of emitting multiple bands of ultraviolet radiation or a broadband of ultraviolet radiation suitable for germicidal purposes. In the past, this has been accomplished by combining different types of glasses in a single lamp that transmits different wavelengths of ultraviolet radiation.

FIG. 1 illustrates one such prior lamp. FIG. 1 schematically illustrates a germicidal lamp 10 having end caps 12 and 14. Placed at either end of the lamp is a stem 16 and 18 for holding leads 20 and 22 supporting a filament 24 and 26. Electrical contact pins 34 and 36 provide an electrical contact through the leads 20 and 22 to the filament or electrodes 24 and 26. A glass envelope or tube is formed of two different types of glass separated by a seam or transition section 32. A first glass tube section 28 is comprised of doped quartz, which transmits ultraviolet radiation of approximately 254 nanometers. A second glass tube or portion 30 comprises quartz that transmits ultraviolet radiation at a wavelength of approximately 185 nanometers. Accordingly, a germicidal lamp having a conventional construction is formed.

In an effort to form a germicidal lamp that can be connected at a single end, a different construction has been made, as illustrated in FIG. 2. In FIG. 2, the germicidal lamp 110 is U-shaped and has end caps 112 and 114 adjacent each other with contact pins 134 and 136. The first glass 128 and the second glass 130 are divided by a seam or transition portion 132. Accordingly, a different type of glass is formed on each leg of the U-shaped germicidal lamp 110.

The germicidal lamps having a seam axially combining two different glass tubes are often difficult to manufacture and align. Also, while these lamps have been useful in providing multiple wavelengths of ultraviolet radiation to provide an effective germicidal action, their size and structure do not readily facilitate widespread use or in applications where a smaller or more compact structure is desired. Additionally, relatively high-powered lamps requiring larger diameter tubing are often difficult to accommodate in a small or compact size. Therefore, there is a need for a compact germicidal lamp that can accommodate glass tubes or cylinders having a relatively large diameter and that may be more easily fabricated.

SUMMARY OF THE INVENTION

The present invention is a compact germicidal lamp comprising a first cylinder or tube of a first type of glass and a second cylinder or tube of a second type of glass placed adjacent and parallel to each other and connected by a perpendicular tube at one end. The first cylinder of the first type of glass is capable of transmitting ultraviolet radiation having a first wavelength, for example, 254 nanometers. The second cylinder or tube of glass is capable of transmitting ultraviolet radiation having a second wavelength, different than the first wavelength, for example, 185 nanometers. The two cylinders or tubes of glass are placed adjacent each other and have electrodes placed at the same end. More than two cylinders may be used with each of the cylinders connected by a perpendicular tube so that the different cylinders or tubes are connected to each other.

Accordingly, it is an object of the present invention to provide a compact, germicidal lamp capable of irradiating multiple wavelengths in a UVC band.

It is another object of the present invention to provide a germicidal lamp that is easily manufactured and customized to provide a predetermined combination of wavelengths and intensity or dose.

It is an advantage of the present invention that a high-powered germicidal lamp can be accommodated in a compact design.

It is another advantage of the present invention that connections can be made at a single end of the germicidal lamp.

It is yet another advantage of the present invention that a relatively long arc length is achieved in a relatively compact space.

It is a feature of the present invention that a perpendicular tube connects adjacent cylinders or tubes of different glass together.

It is another feature of the present invention that a larger diameter tube may be used permitting higher loads, for example greater than approximately 500 watts.

These and other objects, advantages, and features will become readily apparent in view of the following, more detailed description.

DETAILED DESCRIPTION OF THE PREFERRED EMBODIMENTS

Figure 1:
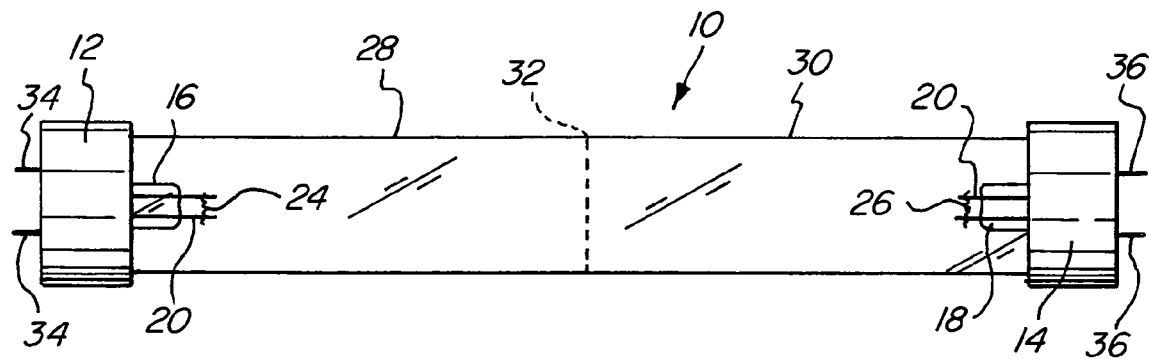
FIG. 1 schematically illustrates a prior art gas discharge germicidal lamp.
Figure 2:
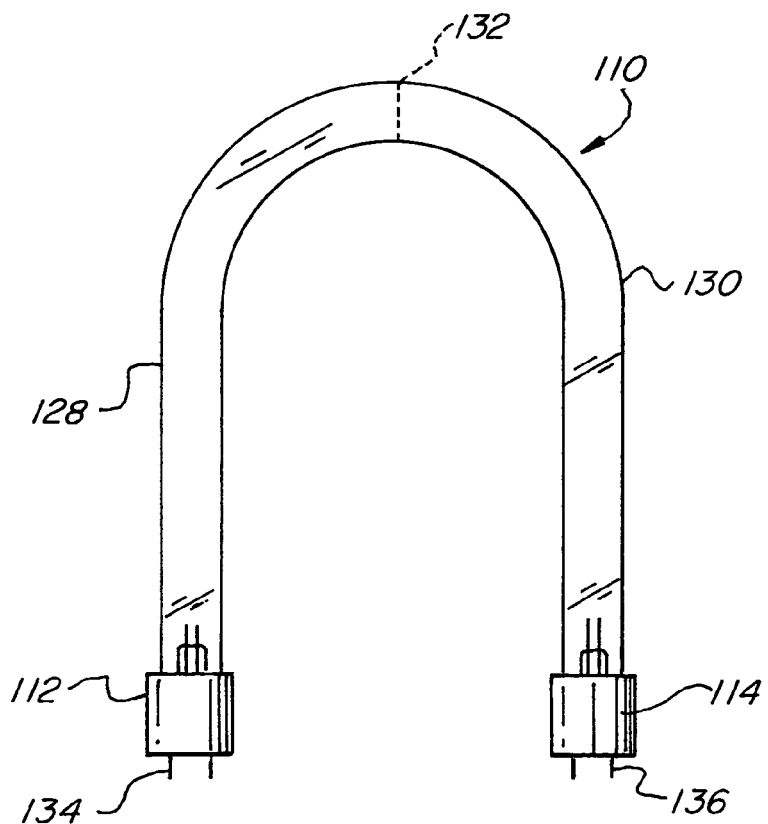
FIG. 2 schematically illustrates a prior art U-shaped gas discharge germicidal lamp.
Figure 3:
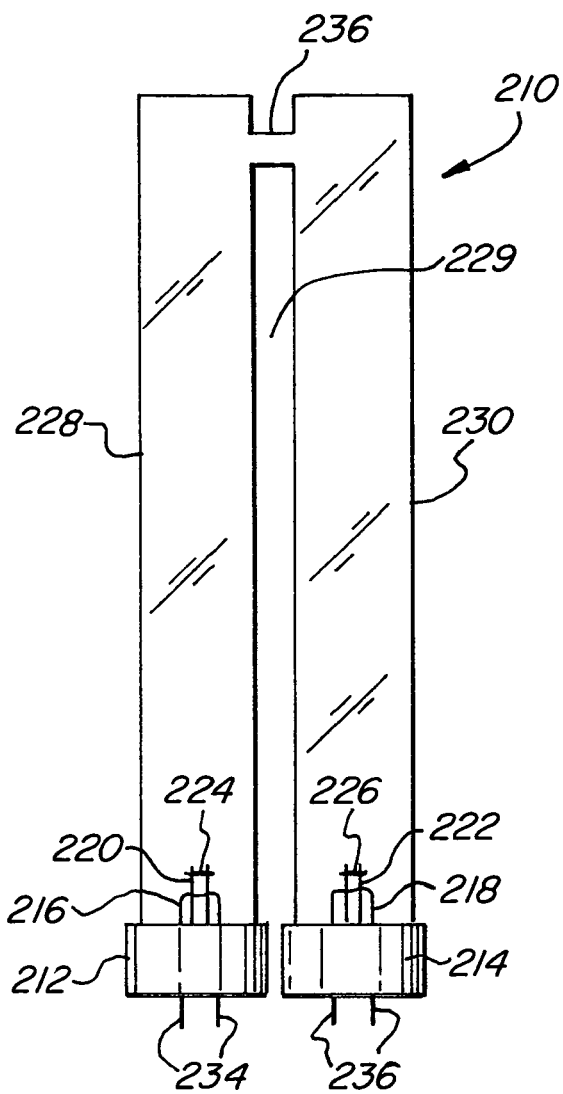
FIG. 3 schematically illustrates a compact gas discharge germicidal lamp of the present invention.

FIG. 3 illustrates a germicidal lamp 210 of the present invention. The germicidal lamp 210 comprises a first glass cylinder or tube 228 made of a first glass material capable of transmitting ultraviolet radiation having a first wavelength. A second glass cylinder 230 is positioned closely adjacent the first glass cylinder 228. The second glass cylinder 230 is made of a second glass material capable of transmitting an ultraviolet radiation having a second wavelength, different than the first wavelength. The first glass material, for example, may be doped quartz for transmitting ultraviolet radiation having a wavelength of approximately 254 nanometers. The second glass material, for example, may be quartz capable of transmitting ultraviolet radiation having a wavelength of approximately 185 nanometers. Other glass material may be used depending upon the specific wavelengths desired.

The first and second glass cylinder 228 and 230 are connected at a top portion thereof by a perpendicular tube 236. Perpendicular tube 236 has a diameter less than the diameter of the first and second glass cylinders 228 and 230. A space 229 separates the substantially parallel first and second glass cylinders 228 and 230. The space 229 is sufficient to provide an effective dose of ultraviolet radiation so as to disinfect the fluid flowing there between. The rate of flow of the fluid and the number of germicidal lamps used may be considered in determining the space 229 sufficient to obtain a desired germicidal action. The germicidal action is generally a function of intensity, exposure time, and wavelength. The space has a dimension that is generally less then a diameter of either one of the first and second glass cylinders 228 and 230. At the other end or bottom of the first and second glass cylinders 228 and 230 are placed end caps 212 and 214. The first and second glass cylinders 228 and 230 are sealed at each end by stems 216 and 218. Placed within the stems 216 and 218 are leads 220 and 222 that are connected to an electrode or filament 224 and 226, respectively. Contact pins 234 and 236 are electrically connected to the leads 220 and 222 and the electrodes or filaments 224 and 226. A gas is placed in each of said first and second glass cylinders for conducting current and creating a discharge when energized. The electrodes 224 and 226, when energize, create an arc there between within the first and second glass cylinders 228 and 230, which are connected together by the tube 236. The arc creates a discharge of ultraviolet radiation. Ultraviolet radiation having a wavelength of approximately 254 nanometers is transmitted through the first glass cylinder 228 and ultraviolet radiation having a wavelength of approximately 185 nanometers is transmitted through the second glass cylinder 230.

Accordingly, the germicidal lamp 210 can be made relatively compact and is capable of transmitting two different wavelengths of ultraviolet radiation capable of effective germicidal action. The present invention is more easily manufactured than other germicidal lamps that require the positioning and coaxial placement of two different tubes of glass material. Additionally, the present invention is capable of providing a much higher-powered germicidal lamp, greater than five hundred watts. The present invention permits the use of a larger diameter cylinder or tube in a much smaller and compact space. Accordingly, the compact design of the present invention facilitates the application of germicidal lamps and their placement in locations that may be suitable for personal type spaces that previously have not been possible or convenient with larger, prior art germicidal lamps.

Figure 4:
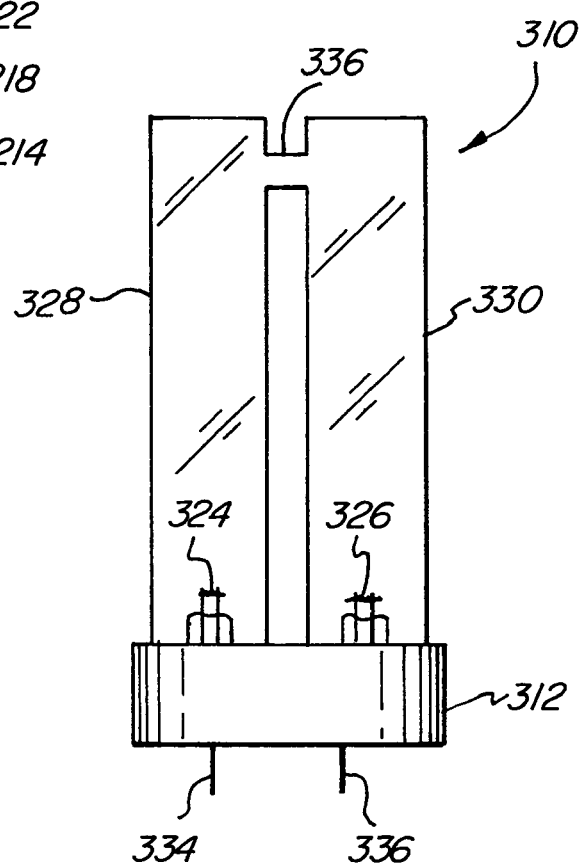
FIG. 4 schematically illustrates another embodiment of a compact germicidal lamp of the present invention.

FIG. 4 illustrates another embodiment of a germicidal lamp 310 of the present invention. In FIG. 4, a first glass cylinder 328 made of doped quartz is connected through perpendicular tube 336 to a second glass cylinder made of quartz. In this embodiment, a single end cap 312 is used in combination with a first contact pin 334 and a second contact pin 336. This results in a single ended lamp having a simplified electrical connection with only two contact pins 334 and 336. The ends of each electrode 324 and 326 may be electrically connected so as to result in only two contact pins 334 and 336.

Figure 5:
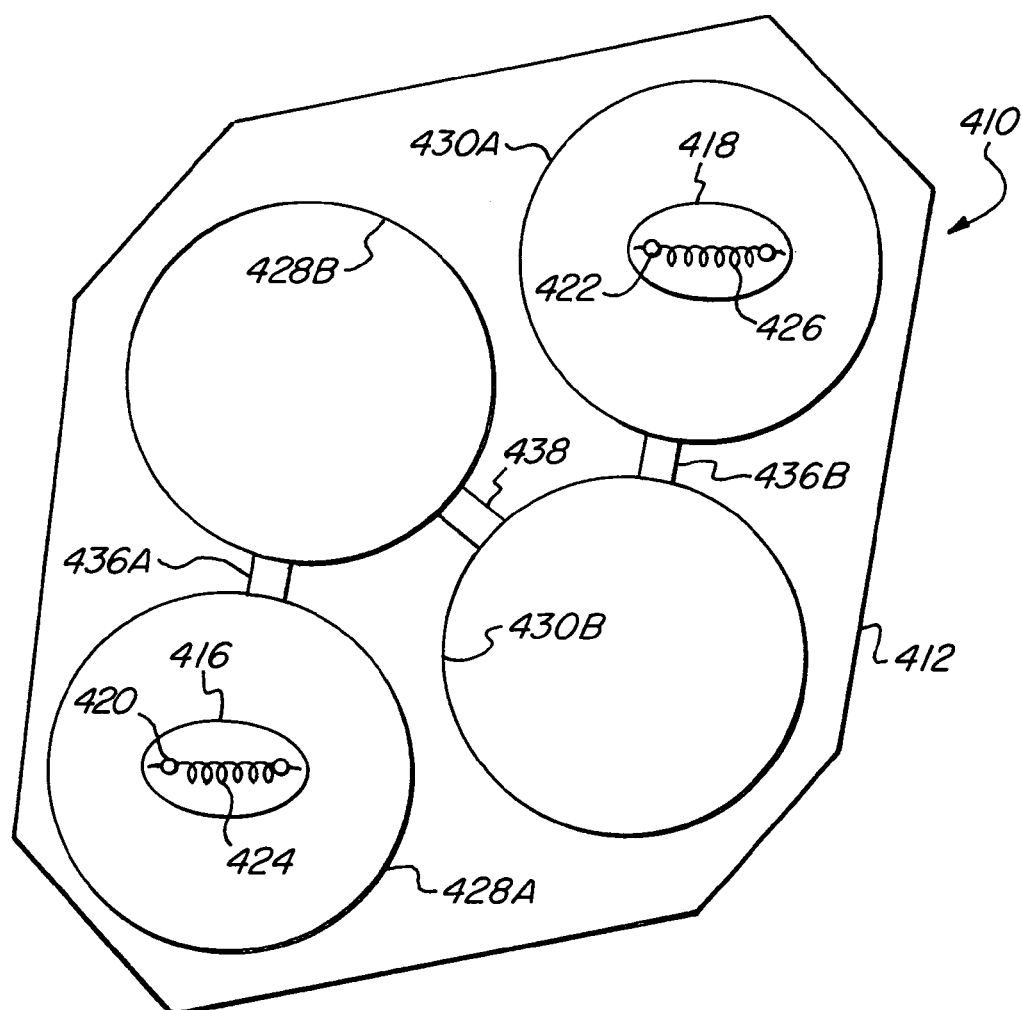
FIG. 5 is a plan view of a compact germicidal lamp of another embodiment of the present invention.

FIG. 5 is a plan view illustrating another embodiment of the present invention utilizing a plurality of cylinders. The germicidal lamp 410 in this embodiment comprises a plurality of glass cylinders 428A, 428B, 430A and 430B. Each of the plurality of cylinders may be made from a different type of glass for transmitting a predetermined wavelength of ultraviolet radiation. For example, cylinders 428A and 428B could be made of doped quartz capable of transmitting ultraviolet radiation having a wavelength of approximately 254 nanometers, and cylinders 430A and 430B may be made of a quartz glass capable of transmitting ultraviolet radiation having a wavelength of approximately 185 nanometers. It should be appreciated that each glass cylinder may be capable of transmitting a band of wavelengths, but is preferably capable of transmitting a band of wavelengths centered about a predetermined wavelength capable of germicidal action.

Glass cylinders 428A and 428B are coupled together by a perpendicular tube 436A placed on the end of the cylinders opposite the electrode 424 formed in a stem 416 and supported by leads 420 within the glass cylinder 428A. Another connecting perpendicular glass tube 438 is formed in a bottom or lower portion of glass cylinders 428B and 430B. Another connecting perpendicular glass tube 436B is formed at a top portion of the glass cylinders 430A and 430B. Within the glass cylinder 430A is placed another electrode 426 within a stem 418 and held by leads 422. An end cap 412 is used to hold the glass cylinders 428A, 428B, 430A, and 430B in position adjacent each other, and to provide the electrical connections to the electrodes 424 and 426.

Accordingly, in this embodiment, an arc is formed between the electrodes 424 and 426. The arc travels to the top of the glass cylinder 428A through the connecting perpendicular tube 436A into glass cylinder 428B through the bottom of the glass cylinder 428B through the connecting perpendicular tube 438 and into the glass cylinder 430B and again out of the connecting perpendicular tube 436B at the top of the glass cylinder 430B and into the top of the glass cylinder 430A to the electrode 426 placed at the bottom of the glass cylinder 430A. The arc length of the germicidal lamp 410 is thereby made relatively long in a very compact space.

Figure 6:
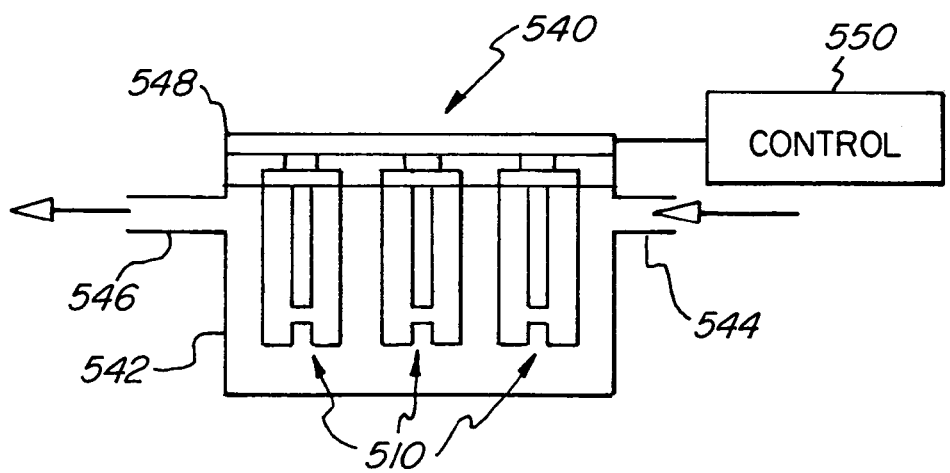
FIG. 6 is schematically illustration a germicidal system for disinfecting or treating a fluid.

FIG. 6 schematically illustrates a germicidal system 540. The germicidal system 540 may be used to purify wastewater or other fluids, such as air. The germicidal system 540 comprises a container 542 having an inlet 544 and an outlet 546. The container 542 is covered with a cover 548. The cover 548 may also act as a fixture for the plurality of different compact germicidal lamps 510 of the present invention. A controller 550 coupled to the cover and fixture 548 controls the operation of the plurality of germicidal lamps 510 depending upon flow of the fluid and germicidal action desired. The present invention has the advantage that a single connection can be made at one end to the germicidal lamp 510. Additionally, the spacing between the cylinders may be such so as to provide a maximum distance in which germicidal action is effective, thereby assuring that fluids flowing between the plurality of cylinders is effectively treated. The plurality of cylinders may also be arranged within the container so as to create a predetermined flow path creating a dose or exposure of a predetermined time for effective germicidal action. The plurality of cylinders may also be positioned so as to create turbulent flow enhancing the germicidal action.

The present invention, in coupling a plurality of relatively closely spaced parallel glass cylinders together, with the glass cylinders providing transmission of different ultraviolet wavelengths, provides a compact germicidal lamp having an effective germicidal action. The use of different glass materials for the glass cylinders makes possible the use of different predetermined wavelengths ideally suited to a particular germicidal application in a single lamp. By the use of different combinations of material for the different glass cylinders, different doses of ultraviolet radiation can be adjusted relatively easily. For example, a greater intensity of a predetermined wavelength may be applied by including more cylinders made from a material transmitting the desired predetermined wavelength. Additionally, the coupling or connecting of the glass cylinders with the perpendicular tubes is an easier manufacturing process than the coaxial joining of glass tubes of different materials. Therefore, the present invention provides a compact germicidal lamp that is relatively easily manufactured at a reduced cost that can be used in a variety of applications that were previously not possible with prior art larger germicidal lamps. The present invention also permits a higher-powered germicidal lamp in a reduced space.

While the present invention has been described with respect to several preferred embodiments, it should readily be appreciated that various modifications may be made without departing from the spirit and scope of the present invention.

What is claimed is:

1. A compact germicidal gas discharge lamp comprising:
   a plurality of glass cylinders positioned substantially parallel to each other, said plurality of glass cylinders comprising at least two different glass materials each capable of transmitting a different wavelength of ultraviolet radiation;
   a tube connecting pairs of said plurality of glass cylinders together;
   a first electrode placed in one end of one of said plurality of glass cylinders; and
   a second electrode placed in one end of another one of said plurality of glass cylinders,
   whereby a compact germicidal lamp having multiple wavelengths capable of more effective germicidal action is formed.

2. A compact germicidal gas discharge lamp as in claim 1 wherein:
   the at least two different glass materials comprise doped quartz and quartz.

3. A compact germicidal gas discharge lamp as in claim 1 wherein:
   the different wavelengths of ultraviolet radiation comprises a first wavelength of 254 nanometers and a second wavelength of 185 nanometers.

4. A compact germicidal gas discharge lamp as in claim 1 wherein:
   the gas discharge lamp has a power greater than 500 watts.

5. A compact germicidal gas discharge lamp as in claim 1 wherein:
   said tube has a diameter less than each of said plurality of glass cylinders.

6. A compact germicidal gas discharge lamp as in claim 1 further comprising:
   a space between each of said plurality of glass cylinders, said space having a dimension sufficient so as to provide effective germicidal action.

7. A compact germicidal gas discharge lamp used for disinfecting a fluid comprising:
   a plurality of first cylinders each made of a first material capable of transmitting ultraviolet radiation having a first wavelength;
   a plurality of second cylinders each made of a second material capable of transmitting ultraviolet radiation having a second wavelength, said plurality of second cylinders placed parallel and adjacent to said plurality of first cylinders;
   a tube placed between pairs of said plurality of first and second cylinders; and
   an electrode placed in an end of two of said plurality of first and second cylinders,
   whereby ultraviolet radiation having different wavelengths is capable of being transmitted exposing the fluid and providing effective germicidal action.

8. A compact germicidal gas discharge lamp used for disinfecting a fluid as in claim 7 wherein:
   the first material comprises doped quartz and the second material comprises quartz.

9. A compact germicidal gas discharge lamp used for disinfecting a fluid as in claim 7 wherein:
   the first wavelength comprises 254 nanometers and the second wavelength comprises 185 nanometers.

10. A compact germicidal gas discharge lamp used for disinfecting a fluid as in claim 7 wherein:
    the gas discharge lamp has a power greater than 500 watts.

11. A compact germicidal gas discharge lamp used for disinfecting a fluid as in claim 7 wherein:
    said tube has a diameter less than each of said plurality of first and second glass cylinders.

12. A compact germicidal gas discharge lamp used for disinfecting a fluid as in claim 7 further comprising:
    a space between each of said plurality of first and second glass cylinders, said space having a dimension sufficient so as to provide effective germicidal action.

13. A compact germicidal gas discharge lamp used for disinfecting a fluid as in claim 12 wherein:
    the space is less than the diameter of either one of said plurality of first and second glass cylinders.

14. A compact germicidal gas discharge lamp used for disinfecting a fluid comprising:
    a plurality of first cylinders each made of a doped quartz material capable of transmitting ultraviolet radiation having a wavelength of approximately 254 nanometers;
    a plurality of second cylinders each made of a quartz material capable of transmitting ultraviolet radiation having a wavelength of approximately 185 nanometers, said plurality of second cylinders placed parallel and adjacent to said plurality of first cylinders, each of said plurality of first and second cylinders being spaced apart to provide an ultraviolet radiation exposure to the fluid so as to provide an effective germicidal action;
    a glass tube placed between pairs of said plurality of first and second cylinders; and
    an electrode placed in an end of two of said plurality of first and second cylinders,
    whereby ultraviolet radiation having different wavelengths is capable of being transmitted through the doped quartz material and quartz material exposing the fluid providing an effective germicidal action.

15. A germicidal system for disinfecting a fluid comprising:
- a container having an inlet and an outlet;
- a fixture placed adjacent said container;
- a control coupled to said fixture;
- a plurality of compact germicidal lamps connected to said fixture and said control, each of said plurality of compact germicidal lamps comprising,
- a plurality of glass cylinders positioned substantially parallel to each other, said plurality of glass cylinders comprising at least two different glass materials each capable of transmitting a different wavelength of ultraviolet radiation;
- a tube connecting pairs of said plurality of glass cylinders together;
- a first electrode placed in one end of one of said plurality of glass cylinders; and
- a second electrode placed in one end of another one of said plurality of glass cylinders,
- whereby the fluid is capable of flowing through said container and around said plurality of glass cylinders causing the fluid to be disinfected.

* * * * *